United States Patent
Hopkins

(10) Patent No.: US 11,701,256 B2
(45) Date of Patent: Jul. 18, 2023

(54) SYSTEMS AND METHODS FOR GAS MIXING IN OCULAR SURGICAL EQUIPMENT

(71) Applicant: Novartis AG, Basel (CH)

(72) Inventor: Mark Alan Hopkins, Mission Viejo, CA (US)

(73) Assignee: Alcon Inc., Fribourg (CH)

( * ) Notice: Subject to any disclaimer, the term of this patent is extended or adjusted under 35 U.S.C. 154(b) by 1197 days.

(21) Appl. No.: 16/271,138

(22) Filed: Feb. 8, 2019

(65) Prior Publication Data

US 2019/0254870 A1 Aug. 22, 2019

Related U.S. Application Data

(60) Provisional application No. 62/633,824, filed on Feb. 22, 2018.

(51) Int. Cl.
*A61F 9/007* (2006.01)
*A61F 9/00* (2006.01)
(Continued)

(52) U.S. Cl.
CPC ........ *A61F 9/00727* (2013.01); *A61F 9/0008* (2013.01); *A61F 9/00736* (2013.01); *A61K 9/0048* (2013.01); *A61K 31/02* (2013.01); *A61K 33/16* (2013.01); *A61M 5/1782* (2013.01); *A61M 13/003* (2013.01); *A61M 37/00* (2013.01); *B65B 3/003* (2013.01); *B65B 31/025* (2013.01); *F17C 5/06* (2013.01);
(Continued)

(58) Field of Classification Search
CPC .. A61M 5/1782; A61M 13/003; A61M 37/00; A61M 2005/006; A61M 2202/02; A61M 2205/3317; A61M 2210/0612; A61F 9/00727; A61F 9/0008; A61F 9/00736; A61K 9/0048; A61K 31/02; A61K 33/16
See application file for complete search history.

(56) References Cited

U.S. PATENT DOCUMENTS

| | | |
|---|---|---|
| 4,813,927 A | 3/1989 | Morris |
| 5,019,037 A | 5/1991 | Wang |

(Continued)

FOREIGN PATENT DOCUMENTS

WO WO2013188595 A1 12/2013

*Primary Examiner* — Lauren P Farrar
(74) *Attorney, Agent, or Firm* — Patterson + Sheridan, LLP

(57) ABSTRACT

A gas mixing system for providing mixed gas for intraocular injection. In some embodiments, a first fixed-volume chamber is automatically purged and filled with gas from a first gas supply input, to a first predetermined pressure. A second fixed-volume chamber is purged and filled with gas from a second gas supply input, to a second predetermined pressure. The first and second predetermined pressures are determined based on a desired concentration of gases in the final mix, and the respective volumes of the first and second fixed-volume chambers and of a third fixed-volume chamber. Gas from the first fixed-volume chamber is then allowed to mix with gas in the third fixed-volume chamber, which was previously purged. Next, gas from the second fixed-volume chamber is allowed to mix with gas in the third fixed-volume chamber. Finally, the mixture of gases in the third fixed-volume chamber is expressed into an intraocular syringe.

7 Claims, 4 Drawing Sheets

(51) Int. Cl.

| | | |
|---|---|---|
| *A61K 9/00* | (2006.01) | |
| *A61K 31/02* | (2006.01) | |
| *A61K 33/16* | (2006.01) | |
| *A61M 5/178* | (2006.01) | |
| *A61M 13/00* | (2006.01) | |
| *B65B 31/02* | (2006.01) | |
| *F17C 5/06* | (2006.01) | |
| *B65B 3/00* | (2006.01) | |
| *A61M 37/00* | (2006.01) | |
| *A61M 5/00* | (2006.01) | |

(52) U.S. Cl.
 CPC ... *A61M 2005/006* (2013.01); *A61M 2202/02* (2013.01); *A61M 2205/3317* (2013.01); *A61M 2210/0612* (2013.01)

(56) References Cited

U.S. PATENT DOCUMENTS

| | | | |
|---|---|---|---|
| 7,713,237 | B2 | 5/2010 | Nazarifar |
| 7,896,839 | B2 | 3/2011 | Nazarifar |
| 8,162,000 | B2 | 4/2012 | Turner |
| 8,312,800 | B2 | 11/2012 | Turner |
| 8,430,840 | B2 | 4/2013 | Nazarifar et al. |
| 8,746,290 | B2 | 6/2014 | Hopkins |
| 8,920,335 | B2 | 12/2014 | Huculak |
| 8,986,242 | B2 | 3/2015 | Auld |
| 9,072,847 | B2 | 7/2015 | Evans |
| 9,241,830 | B2 | 1/2016 | Olivera |
| 9,505,505 | B2 | 11/2016 | Hopkins |
| 9,693,895 | B2 | 7/2017 | Auld |
| 9,764,088 | B2 | 9/2017 | Huculak |
| 10,029,052 | B2 | 7/2018 | Auld |
| 10,434,010 | B2 | 10/2019 | Auld |
| 2007/0038174 | A1 | 2/2007 | Hopkins |
| 2008/0077127 | A1 | 3/2008 | Gao et al. |
| 2008/0103432 | A1* | 5/2008 | Sanchez ............ A61F 9/00736 604/26 |
| 2008/0146988 | A1* | 6/2008 | Olivera ................ F15B 19/005 604/22 |
| 2009/0118680 | A1 | 5/2009 | Goldbrunner |
| 2011/0301539 | A1 | 12/2011 | Rickard |
| 2014/0230956 | A1 | 8/2014 | Hopkins |
| 2017/0333253 | A1 | 11/2017 | Heeren |

\* cited by examiner

SYSTEMS AND METHODS FOR GAS MIXING IN OCULAR SURGICAL EQUIPMENT

PRIORITY CLAIM

This application claims the benefit of priority of U.S. Provisional Patent Application Ser. No. 62/633,824 titled "Systems and Methods for Gas Mixing in Ocular Surgical Equipment," filed on Feb. 22, 2018, whose inventor is Mark Alan Hopkins, which is hereby incorporated by reference in its entirety as though fully and completely set forth herein.

BACKGROUND

In a healthy human eye, the retina is physically attached to the choroid in a generally circumferential manner behind the pars plana. The vitreous humor, a transparent jelly-like material that fills the posterior segment of the eye, helps to cause the remainder of the retina to lie against, but not physically attach, to the choroid.

Sometimes a portion of the retina becomes detached from the choroid. Other times a portion of the retina may tear, allowing vitreous humor, and sometimes aqueous humor, to flow between the retina and the choroid, creating a build-up of subretinal fluid. Both of these conditions result in a loss of vision.

To surgically repair these conditions, a surgeon typically inserts a vitrectomy probe into the posterior segment of the eye via a scleratomy, an incision through the sclera at the pars plana. The surgeon typically also inserts a fiber optic light source and an infusion cannula into the eye via similar incisions, and may sometimes substitute an aspiration probe for the vitrectomy probe. While viewing the posterior segment under a microscope and with the aid of the fiber optic light source, the surgeon cuts and aspirates away vitreous using the vitrectomy probe to gain access to the retinal detachment or tear. The surgeon may also use the vitrectomy probe, scissors, a pick, and/or forceps to remove any membrane that has contributed to the retinal detachment or tear. During this portion of the surgery, a saline solution is typically infused into the eye via the infusion cannula to maintain the appropriate intraocular pressure.

Next, the surgeon may manipulate the detached or torn portion of the retina to flatten against the choroid in the proper location. A soft tip cannula, forceps, or pick is typically utilized for such manipulation. Many surgeons also inject perfluorocarbon liquid as a retinal tamponading fluid into the posterior segment of the eye while aspirating the saline solution in the posterior segment to help cause the detached or torn portion of the retina to flatten against the choroid in the proper location. This procedure is typically referred to as a "fluid/perfluorocarbon" exchange. Other surgeons inject air as a retinal tamponading fluid into the posterior segment of the eye while aspirating the saline solution. This procedure is typically referred to as a "fluid/air" exchange. Finally, other surgeons inject a mixture of air and a gas such as SFO, C3F8, or C2F6 as a retinal tamponading fluid into the posterior segment of the eye while aspirating the saline solution. This procedure is typically referred to as a "fluid/gas" exchange. As used herein, the term "fluid" may refer to any liquid or gas that is suitable for use in the eye, including, but not limited to, saline solution with or without additives, silicone oil, a perfluorocarbon liquid, air, or a perfluorocarbon gas.

The fluid exchange process is most typically performed by using a 60 cc (cubic centimeters) syringe filled with gas. The conventional process of filling the syringe with gas is a manual process that includes mixing the gas with air so that the proportion of gas is between about 10% to 26%, depending on the type of gas used and the expected duration of the gas bubble in the eye. This process may be carried out by first filling the syringe with gas at a concentration of 100% (e.g., from a surgical console with a gas supply), then reducing the volume of gas in the syringe to a specific volume that depends on the target concentration, and then filling the remainder of the syringe with filtered air, thus ending at the target concentration. This manual process, which may involve the use of any of a variety of homemade contraptions, is both time consuming and prone to error.

As a result, a need still exists in vitreoretinal surgery for an improved system for helping to fill syringes with gas to be used in a fluid/gas exchange. For example, the system could allow a scrub nurse to accurately fill the gas syringe to a desired concentration single-handedly, while eliminating or substantially reducing the waste of expensive gas and eliminating time lost as a result of mistakes.

SUMMARY

Described in detail below is a gas mixing system for providing, to a syringe, a mixed gas for intraocular injection. This system may be used to reduce consumable pieces to a very simple, and thus low-cost form—in some embodiments the consumable components may include a syringe and a filter.

In some embodiments, as discussed in further detail below, the gas mixing system includes first and second pressure regulators, each having a regulator input and a regulator output and each being electronically controllable via a respective regulator control input, where the regulator inputs of the first and second pressure regulators have fluidic connections with first and second gas supply inputs, respectively. The gas mixing system further includes first and second fixed-volume chambers having their interior volumes fluidically connected to the regulator outputs of the first and second pressure regulators, respectively, as well as first and second pressure transducers fluidically connected to the interior volumes of the first and second fixed-volume chambers, respectively. First and second shut-off valves, each having a valve input and a valve output, wherein the first and second shut-off valves are fluidically connected to the interior volumes of the first and second fixed-volume chambers, respectively, via their respective first and second valve inputs. These first and second shut-off valves are electrically controllable via respective valve control inputs.

The gas mixing system further includes a first bleed valve with a valve input and a valve output, the valve input being fluidically connected to the interior volume of the first fixed-volume chamber and the valve output being connected to an external environment. This first bleed valve is electrically controllable via a respective valve control input. The system may further include a third fixed-volume chamber (or even further additional chambers) having its interior volume fluidically connected to the valve output of the first shut-off valve and to the valve output of the second shut-off valve. A third pressure transducer is fluidically connected to the interior volume of the third fixed-volume chamber, and a third shut-off valve has a valve input fluidically connected to the interior volume of the third fixed-volume chamber and a valve output, the third shut-off valve being electrically controllable via a valve control input for the third shut-off valve. A second bleed valve has a valve input and a valve output, with the valve input of the second bleed valve being fluidically connected to the interior volume of the third fixed-volume chamber and the valve output of the third bleed valve being connected to the external environment; this second bleed valve is also electrically controllable via a respective valve control input. Finally, a connector is in fluid connection with the valve output of the third shut-off valve, the connector being configured for removably connecting to a filter and intraocular syringe.

Embodiments disclosed herein further include a method of filling a syringe with a retinal tamponading gas. An automatic gas filling consumable containing a syringe is fluidly coupled to a port of an ophthalmic surgical console. A user interface of the console is used to select a particular retinal tamponading gas. The syringe is filled with the retinal tamponading gas from the console. After filling, the syringe is removed from the automatic gas filling consumable for subsequent use by a surgeon.

BRIEF DESCRIPTION OF THE FIGURES

For a more complete understanding of the present embodiments, reference is made to the following description taken in conjunction with the accompanying drawings in which.

It is to be understood that both the foregoing general description and the following detailed description are exemplary and explanatory only and are intended to provide a further explanation of the present embodiments as claimed.

DETAILED DESCRIPTION

Figure 1:
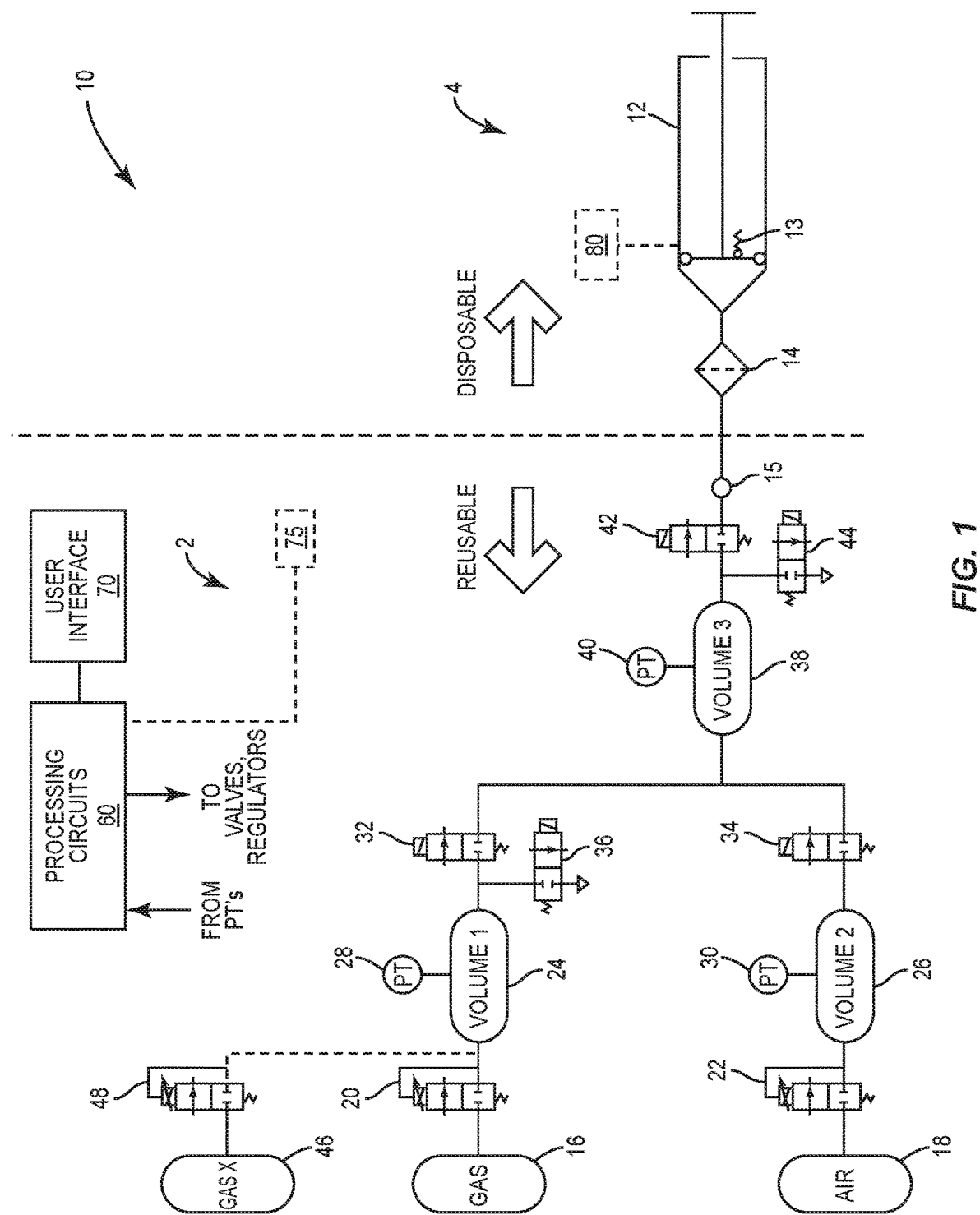
FIG. 1 illustrates an example gas mixing system, according to an embodiment.

FIG. 1 shows an example gas mixing system 10, according to some embodiments. Gas mixing system 10 can be divided into a reusable part 2 and a disposable part 4, with the disposable part 4 comprising a syringe 12, which may include an integral relief valve or filter 13, and a filter 14. Reusable part 2 may include a gas bottle 16 and an air supply 18 (e.g., air bottle or pump for atmospheric air), as well as an assemblage of fixed-volume chambers, electrically controllable regulators and valves, and pressure transducers. As explained in further detail below, reusable part 2 may further include a processing circuit 60 configured to control the regulators and values, based on user input provided via user interface 70 and based on inputs from the various pressure transducers, to automatically and accurately provide a mixture of gas and air, with a desired proportion of gas, to the syringe 12 via a connector 15.

The gas bottle 16 and air supply 18 may be considered to be examples of first and second gas supplies, which are coupled to the rest of the system via first and second gas supply inputs. First and second pressure regulators 20 and 22 each have a regulator input and a regulator output, and each is electronically controllable via a respective regulator control input. The regulator inputs of the first and second pressure regulators 20 and 22 are coupled to the first and second gas supplies (e.g., gas bottle 16 and air supply 18) via first and second gas supply inputs, respectively; the regulator inputs of the first and second pressure regulators 20 and 22 thus have sealed fluidic connections with first and second gas supply inputs, respectively, to which the first and second gas supplies are connected. In some embodiments, a fluidic connection may include a sealed (e.g., pressurizable) connection between two elements, with no intervening valve or regulator. Examples of such fluidic connections are gas-tight tubes or pipes; such a connection may comprise multiple pieces, flanges, and interfaces. Two elements that are "fluidically connected" to one another are thus connected to one another via such a fluid connection.

The reusable part 2 of gas mixing system 10 further includes first and second fixed-volume chambers 24 and 26 having their interior volumes fluidically connected to the regulator outputs of the first and second pressure regulators 20 and 22, respectively. First and second pressure transducers 28 and 30 are fluidically connected to the interior volumes of the first and second fixed-volume chambers 24 and 26, respectively, providing for electrical monitoring of the pressures in chambers 24 and 26.

Gas mixing system 10 further includes first and second shut-off valves 32 and 34, each having a valve input and a valve output. The first and second shut-off valves 32 and 34, which are electrically controllable via respective valve control inputs, are fluidically connected to the interior volumes of the first and second fixed-volume chambers 28 and 30, respectively, via the first and second valve inputs, respectively. A first bleed valve 36, having a valve input and a valve output, is fluidically connected to the interior volume of the first fixed-volume chamber 28, via its valve input, with its valve output being connected to an external environment. The first bleed valve 36 is also electrically controllable via a respective valve control input.

Gas mixing system 10 still further includes a third fixed-volume chamber 38, having its interior volume fluidically connected to the valve output of the first shut-off valve 32 as well as to the valve output of the second shut-off valve 34. A third pressure transducer 40 is fluidically connected to the interior volume of the third fixed-volume chamber, and a third shut-off valve 42 has a valve input fluidically connected to the interior volume of the third fixed-volume chamber 38 and has a valve output, with the third shut-off valve 42 also being electrically controllable via a valve control input. A second bleed valve 44 has a valve input and a valve output, with the valve input of the second bleed valve 44 being fluidically connected to the interior volume of the third fixed-volume chamber 38 and the valve output of the third bleed valve being connected to the external environment. This second bleed valve 44 is also electrically controllable via a respective valve control input.

Finally, gas mixing system 10 includes a connector 15 in fluid connection with the valve output of the third shut-off valve 42. This connector 15 is configured for removably connecting to the filter 14 and intraocular syringe 12.

Although the details of these connections are not shown in FIG. 1, processing circuit 60 may be operatively connected to: the regulator control inputs of the first and second pressure regulators 20 and 22; the valve control inputs of the first, second, and third shut-off valves 32, 34, and 42; the valve control inputs of the first and second bleed valves 36 and 44; the valve control inputs of the first and second bleed valves; and the first, second, and third pressure transducers 28, 30, and 40. Processing circuit 60 may comprise, for example a microcontroller, microprocessor, or the like, coupled to memory and configured to execute appropriate program code stored as software and/or firmware in the memory. In some embodiments, processing circuit 60 may include digital logic specifically designed to carry out some or all of the functionality attributed herein to the processing circuit 60, alone or in combination with a microcontroller/processor and memory storing such program code.

Figure 3:
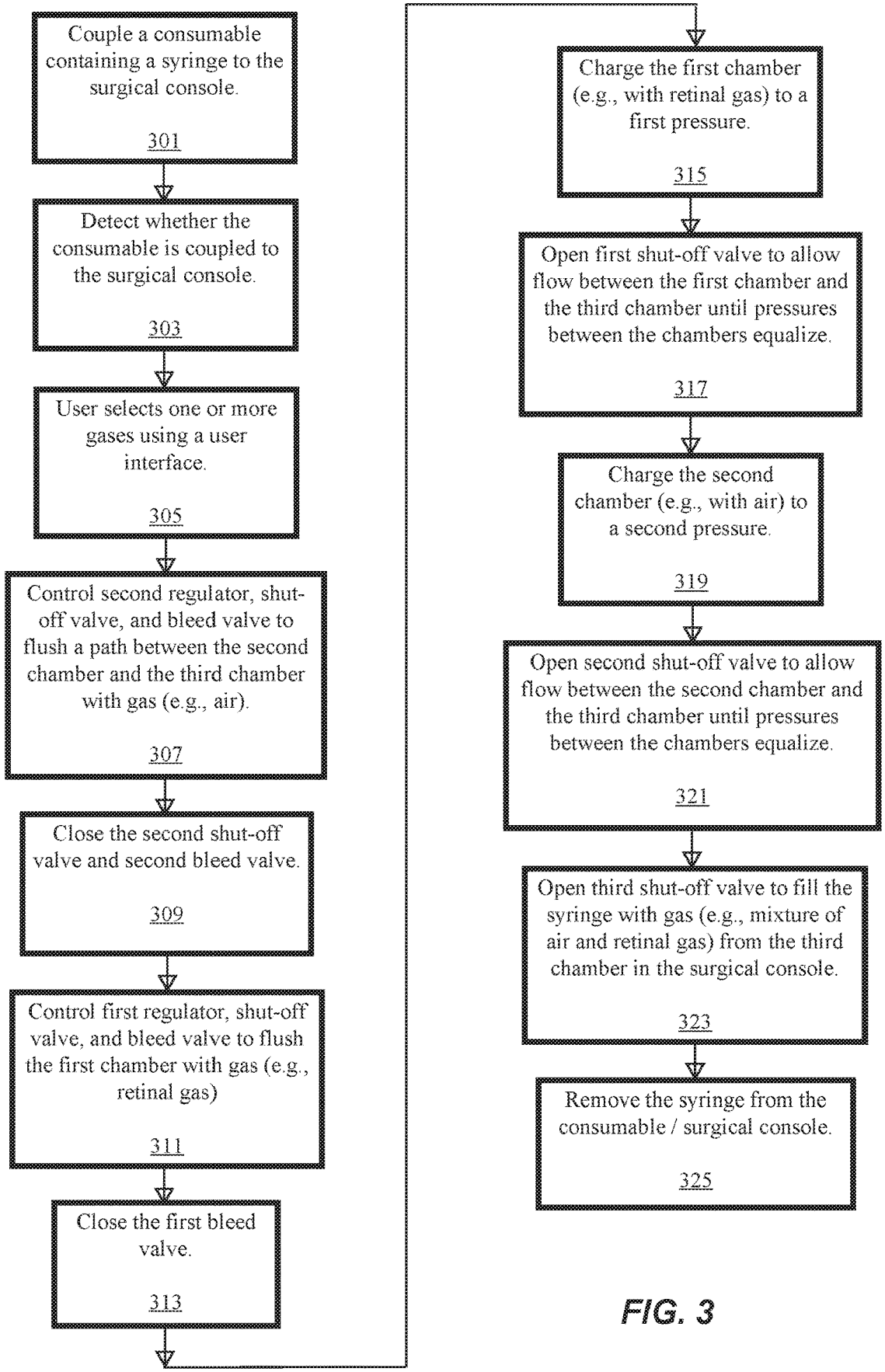
FIG. 3 illustrates a flowchart of a method for filling a syringe with a retinal tamponading gas, according to an embodiment.

FIG. 3 illustrates a flowchart of an embodiment for filling a syringe, according to an embodiment. The elements provided in the flowchart are illustrative only. Various provided elements may be omitted, additional elements may be added, and/or various elements may be performed in a different order than provided below. At 301, an automatic gas filling consumable containing a syringe 12 (and possibly a filter 14 as well) may be fluidly coupled to a connector/port 15 of an ophthalmic surgical console. In some embodiments, the processing circuit 60 is configured to automatically carry out the process starting at 303, after a user attaches the sterile syringe 12/filter 14 assembly to the connector 15. In some embodiments, at 303, the system may automatically detect whether or not the consumable (e.g., containing the syringe 12/filter 14) is coupled to the surgical console, e.g., using a radio-frequency identification (RFID) reader circuit 75 configured to detect the presence of an RFID tag 80, or via the reading of a barcode or similar feature. As another example, a mechanical and/or electrical interlock coupled to the connector 15 might be used to activate a switch or send a signal to indicate to the processing circuit 60 that a properly installed syringe 12 in present.

At 305, a user interface of the console (or, for example, another source of input) may be used to select one or more particular retinal tamponading gases. Other user inputs may also be received through the user interface (e.g., a gas concentration). Other sources of input may include, for example, an RFID tag or other electronically readable tag, a bar code, etc. on the syringe 12 coupled to the console. In some embodiments, the gas mixing system may be configured to "read" a gas type from an attached gas bottle 16, e.g., via an RFID tag or other electronically readable tag, a bar code, or other similar technology, and use this information to verify the user input and/or to prompt the user to ensure that the proper gas is connected.

When a syringe 12 is in place, at 307, the processing circuit 60 is configured to first control the second pressure regulator 22, which in the illustrated system is connected to the air supply 18, the second shut-off valve 34, and the second bleed valve 44 to flush a path between the second fixed-volume chamber 26 and the third fixed-volume chamber 38 with gas from the second gas supply input, thereby purging this path of residual gas or gases from a prior use of the gas mixing system 10. In some embodiments, purging this path may include allowing air to flow from the air supply 18, through pressure regulator 22, chamber 26, valve 34, volume 38, and valve 44 for a predetermined time (other purge techniques are also contemplated). Note that the third shut-off valve 42 may be closed, for this operation (and, for example also shut-off valve 32). At 309, the processing circuit 60 is configured to then close the second shut-off valve 34 and the second bleed valve 44 after said purging; this may be done after a pre-determined time, for example. At 311, the processing circuit 60 is configured to then control the first pressure regulator 20, the first shut-off valve 32, and the first bleed valve 36, to flush the interior volume of the first fixed-volume chamber 24 with gas from the first gas supply input, which in the illustrated system is connected to gas supply 16, thereby purging the interior volume of the first fixed-volume chamber 24 of residual gas or gases from the prior use of the gas mixing system 10. In some embodiments, purging this path may include allowing gas to flow from the gas supply 16, through pressure regulator 20, chamber 24, and valve 36 (but not through closed valve 32) for a predetermined time (other purge techniques are also contemplated). At 313, the processing circuit 60 is further configured to close the first bleed valve 36 (and keep valve 32 closed) after this purging of the interior volume of the first fixed-volume chamber 24. Again, this may be done after a pre-determined time, in some embodiments.

At 315, processing circuit 60 is configured to next control the first pressure regulator 20 to charge the interior volume of the first fixed-volume chamber 24 with gas from the first gas supply input, to a first predetermined pressure, based on feedback from the first pressure transducer 28. As discussed in further detail below, this first predetermined pressure is calculated by processing circuit 60, based on the gas type and the desired concentration of gas in the final mix.

After the interior volume of the first fixed-volume chamber 24 is charged to the first predetermined pressure, as indicated by pressure transducer 28, at 317, the processing circuit 60 opens the first shut-off valve 32, thereby allowing fluid communication between the interior volume of the first fixed-volume chamber 24 and the interior volume of the third fixed-volume chamber 38, and subsequently closes the first shut-off valve 32, after pressures in the first and third fixed-volume chambers are equalized, e.g., as indicated by pressure transducer 40 or after a pre-determined time. In some embodiments, the valve 32 may be closed prior to the chambers equalizing (e.g., the valve 32 may be closed when a target pressure is detected at pressure transducer 40).

At 319, processing circuit 60 is configured to next control the second pressure regulator 22 to charge the interior volume of the second fixed-volume chamber 26 with gas from the second gas supply input, to a second predetermined pressure, based on feedback from the second pressure transducer 30. Note that in the illustrated example, an air supply 18 is attached to the second gas supply input, to provide for the mixing of the gas from gas bottle 16 with air, from air supply 18. Again, as discussed in further detail below, this second predetermined pressure is calculated by processing circuit 60, based on the gas types (in gas bottle 16 and air supply 18) and the desired concentrations of gas in the final mix. It will be appreciated, of course, that the system is more generally applicable, and gases other than air may be used here or with other gas supply inputs.

After the interior volume of the second fixed-volume chamber 26 is charged to the second predetermined pressure, at 321, the processing circuit 60 opens the second shut-off valve 34, thereby allowing fluid communication between the interior volume of the second fixed-volume chamber 26 and the interior volume of the third fixed-volume chamber 38. This allows the gases in the second and third fixed-volume chambers 26 and 38 to mix and for the pressures to equalize (at which point, shut-off valve 34 may be closed). In some embodiments, the shut-off valve 34 may be closed before the pressures equalize (for example, if a target pressure is detected at pressure transducer 40 or after a pre-determined time).

At 323, the syringe 12 may be filled with the retinal tamponading gas from the console. For example, once pressures in the second and third fixed-volume chambers are equalized, e.g., as indicated by pressure transducer 40 (or, for example, when a target pressure is detected at pressure transducer 40 or after a pre-determined time), the processing circuit 60 may open the third shut-off valve 42, thereby enabling mixed gases from the interior volume of the third fixed-volume chamber 38 to flow to the connector 15, and thence through filter 14 into syringe 12, pushing the plunger back as pressure is increased and gas enters. In some embodiments, as illustrated in FIG. 1, the syringe 12 may have an integrated relief valve 13, or alternately a filter, that allows any excess gas pressure to be relieved from the syringe 12. This also facilitates a purging of the syringe 12 to ensure that any air previously in the syringe 12 has been expressed out of the syringe 12. Note that the volume of third fixed-volume chamber 38 should be sufficient to ensure that when the syringe 12 is filled with the gas mixture from the third fixed-volume chamber 38, there is ample volume to both purge the syringe 12 of any air that was in it, and fill the syringe completely with the appropriate gas concentration.

At 325, after filling, the syringe is removed from the automatic gas filling consumable (and the surgical console) for subsequent use by a surgeon. For example, once the syringe 12 is loaded with the gas mixture via shut-off valve 42 and connector 15, the user can disconnect the syringe 12 from the filter 14, attach a new filter to the syringe 12, and then connect the syringe to a suitable device for expressing the gas mixture into patient's eye.

It will be appreciated that given the respective fixed volumes of fixed-volume chambers 24, 26, and 38, appropriate first and second pressures for charging the first and second fixed-volume chambers 24 and 26 with gas and air, respectively, can be determined using well-known relationships between partial pressures, mole fractions, and volumes, for any desired concentration of gas, relative to the final air and gas mix in the third fixed-volume chamber 38. The use of fixed volumes in the system minimizes the variability of the system.

Processing circuit 60 may thus be configured with an appropriate algorithm for calculating the first and second pressures based on the respective volumes of the fixed-volume chambers, the desired concentration, e.g., as input by a user via the user interface 70, and the properties of the gas. In some embodiments, (e.g., as noted at 305) the user inputs the gas type, as well as the gas concentration, via the user interface. In other embodiments, the disposable unit, may convey information regarding the desired concentration and/or the gas type, via an RFID tag or other electronically readable tag, a bar code, etc. In some embodiments, the gas mixing system may be configured to "read" a gas type from an attached gas bottle 16, e.g., via an RFID tag or other electronically readable tag, a bar code, or other similar technology, and use this information to verify the user input and/or to prompt the user to ensure that the proper gas is connected.

Figure 4:
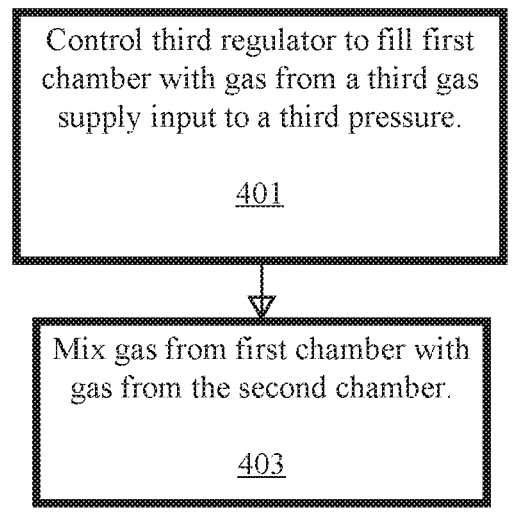
FIG. 4 illustrates a flowchart of an extended method for utilizing a third gas, according to an embodiment.

It will be further appreciated that the gas mixing system 10 described above may be extended to allow for the mixing of more than two gases. In FIG. 1, gas mixing system 10 thus includes a third gas supply input, with gas bottle 46 coupled to it. A third pressure regulator 48, which is electrically controllable like the other pressure regulators described above, has its input in fluid communication with the third gas supply input, and its output in fluid communication with the first fixed-volume chamber 24. With this configuration, after the first-fixed volume chamber 24 is purged and filled (at 311-315) to the first predetermined pressure discussed above with gas from gas bottle 16, via the first regulator 20, at 401, the third regulator 48 can be electrically controlled by processing circuit 60, e.g., based on feedback from pressure transducer 28, to further fill the first fixed-volume chamber 24 with gas from the third gas supply input, to a third predetermined pressure. This third predetermined pressure, which necessarily exceeds the first predetermined pressure, can be calculated based on the gas types provided via the first and third gas supply inputs (from gas bottles 16 and 46, respectively) and desired concentrations of the gases in the final mixture. After the first fixed-volume chamber 24 is thus filled to the third predetermined pressure with a mixture of gases from gas bottles 16 and 46, at 403, the gases in the first fixed volume-chamber 24 can be mixed with the pressurized gas (air) from the second fixed-volume chamber 26, in the same manner as described above (see 317 to 321), resulting in a three-way combination, in the third fixed-volume chamber 38, of gases from the first, second, and third gas supply inputs. Thus, the process in FIG. 3 can be modified by adding elements 401 and 403 of FIG. 4 in between elements 313 and 317 to provide a process for the mixing of more than two gases. Resuming at 323, this mixture can be subsequently released into the syringe 12, as described above. Again, one of these three gas inputs is typically air, but need not be in every implementation or use.

Figure 2:
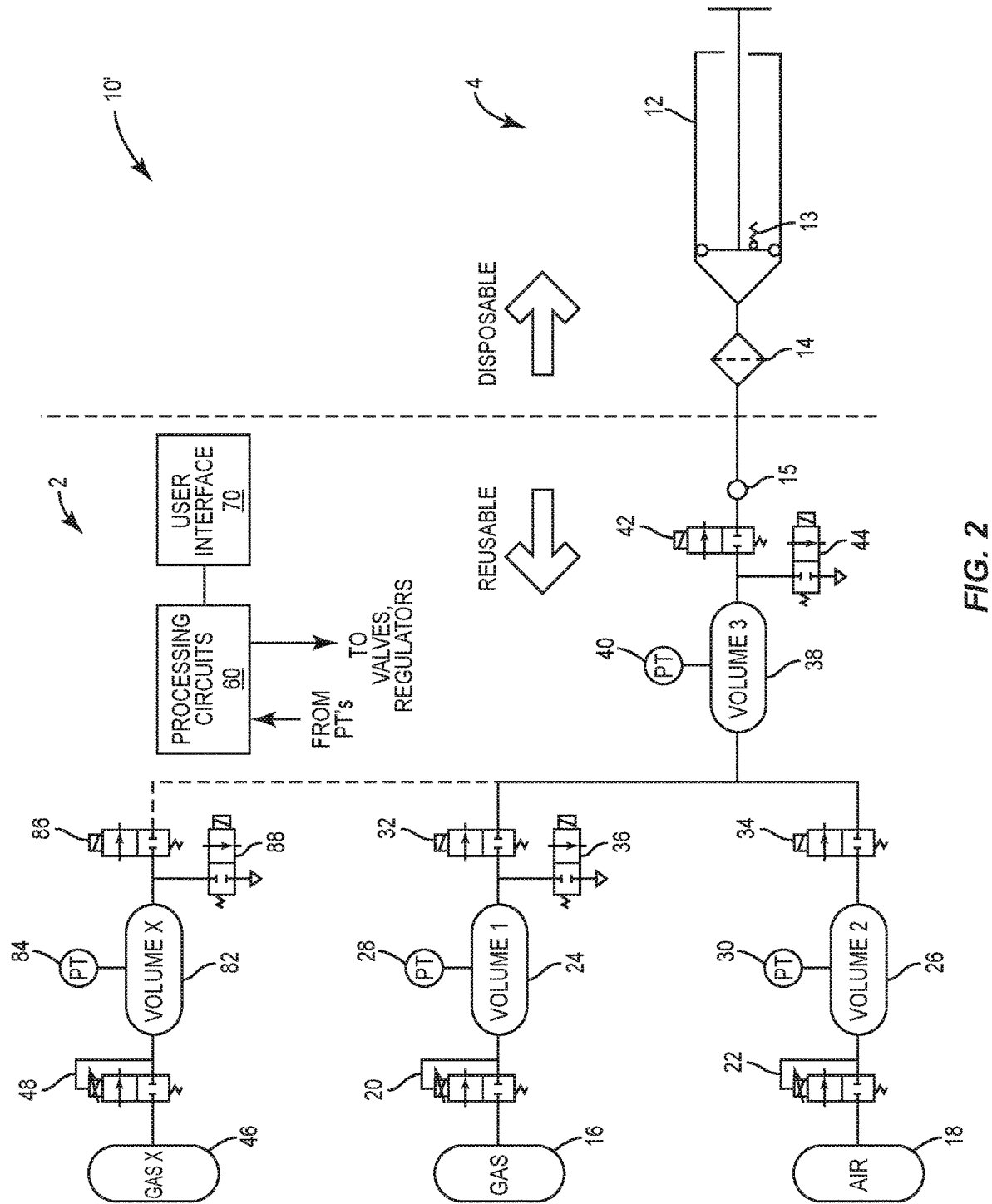
FIG. 2 illustrates an alternative approach to extending the gas mixing system for mixing more than two gases, according to an embodiment.

In FIG. 2, the reusable part 2 of gas mixing system 10' includes a fourth fixed-volume chamber 82 and a fourth pressure transducer 84 fluidically connected to the interior volume of the fourth fixed-volume chamber 82. In gas mixing system 10', the output of the third pressure regulator 48 is in fluid communication with the interior volume of the fourth fixed-volume chamber 82, rather than with the first fixed-volume chamber 24.

Gas mixing system 10' further includes a fourth electrically controllable shut-off valve 86, with its input fluidically connected to the interior volume of the fourth fixed-volume chamber 82 and its output fluidically connected to the interior volume of the third fixed-volume chamber 38, along with the outputs from the first and second shut-off valves 32 and 34. A third electrically controlled bleed valve 88 has its input fluidically connected to the interior volume of the fourth fixed-volume chamber 82 and its output connected to the external environment.

Figure 5:
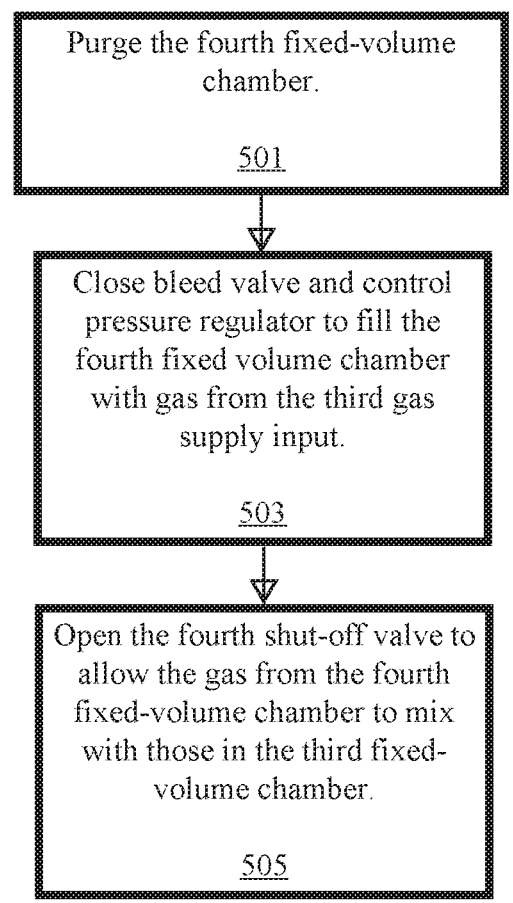
FIG. 5 illustrates a flowchart of an alternate method for utilizing a third gas, according to an embodiment.

In operation, at 501 (see FIG. 5), the processing circuit 60 may purge the fourth fixed-volume chamber 82 in a similar manner to that in which it purges the first fixed-volume chamber 24, i.e., by opening the third bleed valve 88 (while the fourth shut-off valve 86 is closed) and controlling the pressure regulator 48 to allow gas to flow from the third gas supply input through the fourth fixed-volume chamber 82 to the external environment, via the bleed valve 88. After the fourth fixed-volume chamber 82 is purged, at 503, processing circuit 60 closes bleed valve 88, and controls the pressure regulator 48 to fill the fourth fixed-volume chamber 82 with gas from the third gas supply input to a pre-determined pressure, e.g., based on feedback from pressure transducer 84, where this pre-determined pressure, like the others discussed herein, is calculated based on the desired concentrations of gases in the final mix and the types of gases in use.

After gases from the first and second gas supply inputs have been mixed in the third fixed-volume chamber 38 as described above for gas mixing system 10 (see 307 to 321), the processing circuit 60, at 505, may open the fourth shut-off valve 86 (e.g., after closing shut-off valves 32 and 34), thus allowing the gas from the fourth fixed-volume chamber 82 to mix with those in the third fixed-volume chamber 38, again providing for a three-way combination, in the third fixed-volume chamber 38, of gases from the first, second, and third gas supply inputs. This mixture can be subsequently released into the syringe 12, as described above at 323. Once more, one of these three gas inputs is typically air, but need not be in every implementation or use.

The schematics shown in FIGS. 1 and 2 represent examples of gas mixing systems according to the presently disclosed techniques, and may be considered as examples. Additional features and functions and redundancy can be added to improve performance and/or the safety of the system. In some embodiments, for example, the illustrated pressure sensors/transducers may continuously monitor pressures throughout the system to ensure the system is behaving as expected, so that the system can be shut down at any time to prevent the incorrect gas concentration from being delivered. Additional sensors may be monitored as well. As discussed above, the system can be designed to be scalable, where additional gases can be added to the system to allow for multiple gases being available to the user. Gases that can be used with the system may include SF6, C3F8, and C2F6 (but is not limited to those gases).

From the above, it may be appreciated that the present embodiments provide an improved systems and methods for helping to fill a syringe with gas and helping to perform fluid/gas exchanges in vitreoretinal surgery. The system allows a scrub nurse to fill a gas syringe single handed, allows the nurse to maintain the integrity of the sterile field, eliminates the waste of expensive gas, and saves time lost due to mistakes.

It is believed that the operation and construction of the present embodiments will be apparent from the foregoing description. While the systems and methods shown or described above provide example embodiments, various changes and modifications may be made therein without departing from the spirit and scope of the following claims.

What is claimed is:

1. A method, comprising:
    fluidly coupling an automatic gas filling consumable containing a syringe to a port of an ophthalmic surgical console;
    selecting a particular retinal tamponading gas;
    charging an interior volume of a first fixed-volume chamber to a first predetermined pressure, wherein the interior volume of the first fixed volume chamber is charged based on a size of the interior volume and a relationship between gases in the retinal tamponading gas;
    filling the syringe with the retinal tamponading gas from the console; and
    after filling, the syringe is removed from the automatic gas filling consumable for subsequent use by a surgeon,
    wherein the ophthalmic surgical console comprises:
        a first pressure regulator;
        a second pressure regulator;
        a third pressure regulator;
        a first shut-off valve;
        a second shut-off valve;
        a third shut-off valve;
        a first bleed valve;
        a second bleed valve;
        a third bleed valve;
        a first gas input;
        a second gas input; and
        a third gas input; and
    wherein filling the syringe with the retinal tamponading gas comprises:
        controlling the second pressure regulator, the second shut-off valve, and the second bleed valve to flush a path between a second fixed-volume chamber and a third fixed-volume chamber with gas from the second gas supply input, thereby purging said path of residual gas or gases from a prior use of the ophthalmic surgical console;
        closing the second shut-off valve and the second bleed valve after said purging;
        controlling the first pressure regulator, the first shut-off valve, and the first bleed valve to flush the interior volume of the first fixed-volume chamber with gas from the first gas supply input, thereby purging the interior volume of the first fixed-volume chamber of residual gas or gases from the prior use of the ophthalmic surgical console; and
        closing the first shut-off valve and the first bleed valve after said purging of the interior volume of the first fixed-volume chamber.

2. A method, comprising:
    fluidly coupling an automatic gas filling consumable containing a syringe to a port of an ophthalmic surgical console;
    selecting a particular retinal tamponading gas;
    charging an interior volume of a first fixed-volume chamber to a first predetermined pressure, wherein the interior volume of the first fixed volume chamber is charged based on a size of the interior volume and a relationship between gases in the retinal tamponading gas;
    filling the syringe with the retinal tamponading gas from the console; and
    after filling, the syringe is removed from the automatic gas filling consumable for subsequent use by a surgeon,
    wherein the ophthalmic surgical console comprises:
        a second fixed-volume chamber; and
        a third fixed volume chamber; and
    wherein filling the syringe with the retinal tamponading gas comprises:
        controlling a first pressure regulator to charge the interior volume of the first fixed-volume chamber with gas from a first gas supply input, to a first predetermined pressure, based on feedback from a first pressure transducer;
        after the interior volume of the first fixed-volume chamber is charged to the first predetermined pressure, opening a first shut-off valve, thereby allowing fluid communication between the interior volume of the first fixed-volume chamber and an interior volume of the third fixed-volume chamber; and
        closing the first shut-off valve, after pressures in the first fixed-volume chamber and the third fixed-volume chamber are equalized.

3. The method of claim 2, wherein filling the syringe with the retinal tamponading gas further comprises:
    controlling a second pressure regulator to charge an interior volume of the second fixed-volume chamber with gas from a second gas supply input, to a second predetermined pressure, based on feedback from a second pressure transducer;
    after the interior volume of the second fixed-volume chamber is charged to the second predetermined pressure, opening a second shut-off valve, thereby allowing fluid communication between the interior volume of the second fixed-volume chamber and the interior volume of the third fixed-volume chamber; and
    after pressures in the second fixed-volume chamber and the third fixed-volume chamber are equalized, opening a third shut-off valve, thereby enabling mixed gases from the interior volume of the third fixed-volume chamber to flow to the port of the ophthalmic surgical console coupled to the syringe.

4. The method of claim 3, further comprising performing said opening of the third shut-off valve, after pressures in the second and third fixed-volume chambers are equalized, responsive to detecting that an intraocular syringe is connected to the port of the ophthalmic surgical console coupled to the syringe.

5. The method of claim 2, wherein the first predetermined pressure is calculated based on user input from a user interface.

6. The method of claim 2, wherein a desired gas concentration is determined based on information obtained from an intraocular syringe connected to the port of the ophthalmic surgical console coupled to the syringe, via an electrical or radio-frequency (RF) with a component in or attached to the intraocular syringe, and the first predetermined pressure is calculated based on the desired gas concentration.

7. A method, comprising:
- fluidly coupling an automatic gas filling consumable containing a syringe to a port of an ophthalmic surgical console, wherein the ophthalmic surgical console comprises:
  - a first pressure regulator;
  - a second pressure regulator;
  - a third pressure regulator;
  - a first gas supply input;
  - a second gas supply input;
  - a third gas supply input;
  - a first fixed-volume chamber
  - a second fixed-volume chamber; and
  - a third fixed-volume chamber;
- selecting a particular retinal tamponading gas;
- filling the syringe with the retinal tamponading gas from the console, wherein filling the syringe with the retinal tamponading gas further comprises:
  - controlling the first pressure regulator to charge the interior volume of the first fixed-volume chamber with gas from the first gas supply input, to the first predetermined pressure, based on feedback from a first pressure transducer;
  - controlling the third pressure regulator to further charge the interior volume of the first fixed-volume chamber with gas from the third gas supply input;
  - after the interior volume of the first fixed-volume chamber is charged with gas from the first gas supply input and gas from the third gas supply input, opening a first shut-off valve, thereby allowing fluid communication between the interior volume of the first fixed-volume chamber and an interior volume of the third fixed-volume chamber;
  - closing the first shut-off valve, after pressures in the first fixed-volume chamber and the third fixed-volume chamber are equalized;
  - controlling the second pressure regulator to charge an interior volume of the second fixed-volume chamber with gas from the second gas supply input, to a second predetermined pressure, based on feedback from a second pressure transducer;
  - after the interior volume of the second fixed-volume chamber is charged to the second predetermined pressure, opening a second shut-off valve, thereby allowing fluid communication between the interior volume of the second fixed-volume chamber and the interior volume of the third fixed-volume chamber; and
  - after pressures in the second fixed-volume chamber and the third fixed-volume chamber are equalized, opening a third shut-off valve, thereby enabling mixed gases from the interior volume of the third fixed-volume chamber to flow to the port of the ophthalmic surgical console coupled to the syringe; and
- after filling, the syringe is removed from the automatic gas filling consumable for subsequent use by a surgeon.

* * * * *